United States Patent [19] [11] 4,282,240
Baldwin et al. [45] Aug. 4, 1981

[54] AMINO SUBSTITUTED TETRAHYDROBENZINDOLES

[75] Inventors: John J. Baldwin, Lansdale; James H. Jones; George F. Lundell, both of Blue Bell, all of Pa.

[73] Assignee: Merck & Co., Inc., Rahway, N.J.

[21] Appl. No.: 96,948

[22] Filed: Nov. 23, 1979

[51] Int. Cl.³ .................... A61K 31/40; C07D 209/90
[52] U.S. Cl. .............................. 424/274; 260/326.27; 260/326.5 B; 260/326.9
[58] Field of Search ...................... 260/326.5 B, 326.9; 424/274

[56] References Cited

U.S. PATENT DOCUMENTS

| 3,200,130 | 8/1965 | Szmuszkovicz | 260/326.9 |
| 4,110,339 | 8/1978 | Bach et al. | 260/326.5 B |

OTHER PUBLICATIONS

Stoll et al., Chem. Abs., vol. 46:1539f–1540d (1959).
Stoll et al., Chem. Abs., vol. 47:2167d (1953).
Bach et al.; J. Med. Chem., vol. 17; pp. 312–313 (1974).
Bowman et al., J.C.S. Perk. I. pp. 438–442 (1973).
Harris et al., Chem. Abs., vol. 54:12367f (1960)

Primary Examiner—Mary C. Lee
Attorney, Agent, or Firm—Daniel T. Szura; Harry E. Westlake, Jr.

[57] ABSTRACT

Aminosubstituted tetrahydrobenzindoles having antihypertensive activity are disclosed.

8 Claims, No Drawings

AMINO SUBSTITUTED TETRAHYDROBENZINDOLES

BACKGROUND OF THE INVENTION

The present invention is concerned with certain aminosubstituted tetrahydrobenzindoles, their preparation and pharmaceutical use.

Tetrahydrobenzindoles of the formulae

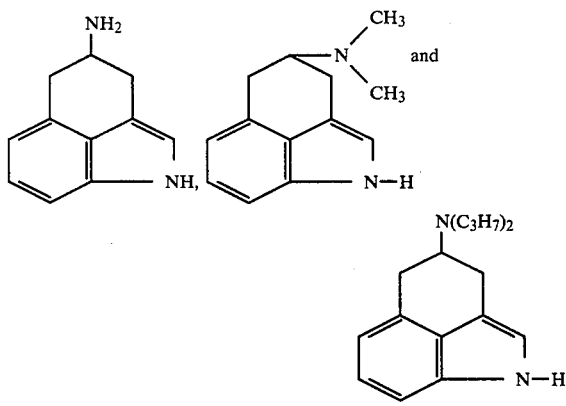

are disclosed in U.S. Pat. No. 4,110,339. No antihypertensive activity is suggested.

The structural feature

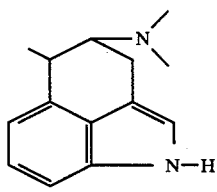

is also disclosed by Bach et al in J. Med. Chem. 17, 312-314 (1974). However, no specific substituents at the open bonds are suggested. No antihypertensive activity is suggested.

A novel series of aminosubstituted tetrahydrobenzindoles has been discovered. The compounds have pharmacological activity, e.g. antihypertensive, prolactin inhibition, anti-Parkinson agent.

SUMMARY OF THE INVENTION

Aminosubstituted tetrahydrobenzindoles of the formula

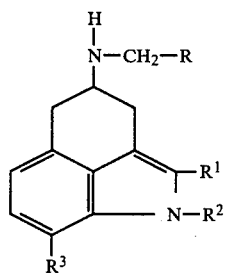

have been discovered.

DESCRIPTION OF THE PREFERRED EMBODIMENTS

An embodiment of the present invention is compounds of the formula

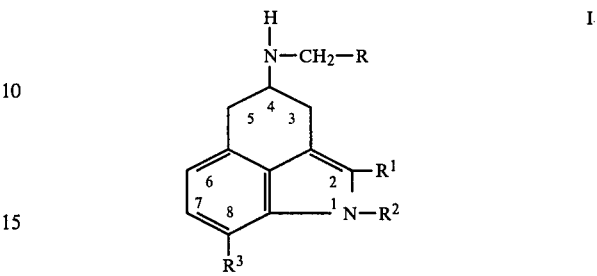

and pharmaceutically acceptable salts thereof wherein
$R_1$ is H, alkyl or aryl
$R^1$ is H or halogen
$R^2$ is H, alkyl or aralkyl and
$R^3$ is H, OH, halogen, $OCH_3$ or $C_1$-$C_3$alkyl.

The positions on the I ring structure are numbered as indicated.

The term alkyl includes straight and branched chain alkyls having up to 6 carbon atoms. Alkyl of 1 to 3 carbon atoms, e.g. methyl, isopropyl, ethyl and the like are preferred. The term aryl includes hydrocarbon aryl groups and especially those containing 6 carbon atoms in the aryl ring. Phenyl and monsubstituted phenyl groups wherein the substituents are halogen, $C_1$-$C_3$alkyl or $C_1$-$C_3$alkoxy are preferred aryl groups. Examples of such groups are chlorophenyl, iodophenyl, methoxyphenyl,isopropoxyphenyl, n-propylphenyl and the like. The term aralkyl includes phenyl-and monosubstitutedphenyl-$C_1$-$C_3$-alkyl group. The preferred substituted phenyl group is the same as that defined by the term aryl above. Examples of aralkyl groups are benzyl, bromophenyl-$C_3H_6$—, ethoxyphenyl -$C_2H_4$, methylphenyl-$CH_2$— and the like. The term halogen includes Br, Cl, F and iodo with Br, Cl and F being preferred and Br and Cl being more preferred.

The pharmaceutically acceptable salts are the salts of formula I with suitable inorganic or organic acids. Examples of useful organic acids are carboxylic acids such as acetic acid, fumaric acid, maleic acid, succinic acid, pamoic acid, pivalic acid and oxalic acid and non carboxylic acid such as isethionic acid naphthalene disulfonic acid and the like. Useful inorganic acids are the hydrohalides such as HCl and HBr, $H_2SO_4$, phosphoric acid and the like.

One class of preferred compounds has the formula

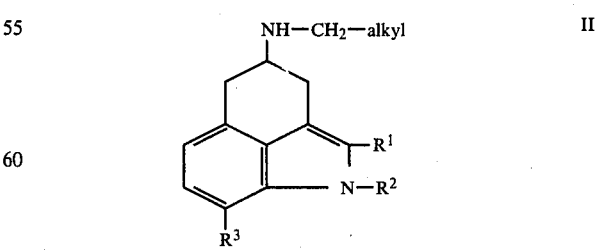

In preferred compounds of formula II, alkyl is $C_1$-$C_3$alkyl, preferably methyl and $R^2$ is H. In a most preferred formula II compound, Alkyl is $CH_3$ and $R^1$, $R^2$, and $R^3$ are all H.

Another class of preferred compounds has the formula

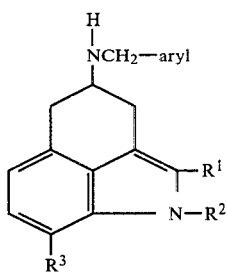

In preferred compounds of formula III, $R^2$ is H. In a more preferred formula III compound, aryl is phenyl and $R^1$, $R^2$ and $R^3$ are all H.

The compounds of the present invention are active antihypertensives. A representative compound was tested in a protocol using a spontaneously hypertensive (SH) rat model to demonstrate this activity. This test indicates that the present compounds would be useful in treating hypertension in hypertensive human patients.

The compounds of the present invention are administered to the hypertensive patient by any convenient mode of administration e.g. orally or parenterally using appropriate dosage e.g. tablets, emulsions, solutions, capsules for oral administration and solutions, suspensions, emulsions for parenteral administration. Conventional procedures are used to prepare suitable pharmaceutical compositions in proper dosage forms using conventional, pharmaceutically acceptable diluents, compounding ingredients, and the like. Sufficient amount of a compound of the present invention is administered to the patient to produce the desired therapeutic effect i.e. lowering of high blood pressure. Suitable dosages will thus vary and the daily dosage in humans may range from about 10 mg. to about 3000 mg., preferably about 20 mg. to about 1000 mg. and more preferably about 50 mg. to about 500 mg.

The present compounds also have other pharmacological properties which make them useful in humans as prolactin inhibitors or for treating Parkinson's disease, at appropriate dosages and using appropriate modes of administration e.g. parenterally or orally.

The compounds of the present invention may be prepared by any available process. A convenient process useful for this preparation is illustrated by the following set of equations: the term tos stands for the tosylate or p-tolysulphonyl moiety.

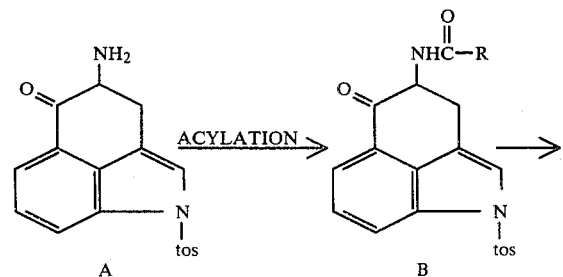

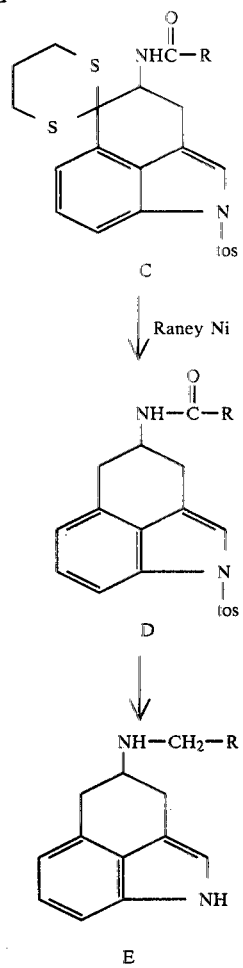

The compound A is known [see Bowman et al., J. C. S. Perkin I, 438 (1973)]. Acylation of A with a suitable anhydride or acyl halide introduces the

substituent on the amino N (compound B). The ketone group adjacent to the amino group is then thioketalized by treatment with 1,3-propanedithiol and trimethylsilylchloride in chloroform using conventional conditions to yield the C product. The thioketal group is removed by treatment with a suitable catalyst such as Raney nickel to yield compound D. The product (D) obtained is then hydrogenated using an appropriate system such as lithum aluminum hydride to yield the desired final product E.

The following example illustrates preparation of representative compounds of the present invention. Temperatures are in degrees Celcius.

EXAMPLE 1

4-(N-ethylamino)-1,3,4,5-Tetrahydrobenz[c,d]Indole

Step A: 4-Acetamino-1,3,4,5-tetrahydro-1-(p-tolysulphonyl)benz[c,d]indol-5-one

A heterogeneous mixture of 4-amino-1,3,4,5-tetrahydro-1-(p-tolysulphonyl)benz[c,d]indol-5-one hydrochloride (10 gms) and acetic anhydride (100 ml) is heated on a steam bath until homogeneity is achieved (15 minutes). The reaction mixture is poured with stirring into water (650 ml). The solid is filtered and dried in a steam oven to yield 9.5 gms of 4-acetamino-1,3,4,5-tetrahydro-1-(p-tolylsulphonyl)benz[c,d]indol-5-one, m.p. 180°-185°.

Step B: 4-Acetamino-1,3,4,5-tetrahydro-1-(p-tolylsulphonyl)benz[c,d]indol-5-one(1,3-propylenedi-thio Ketal)

To a stirred mixture of 4-acetamino-1,3,4,5-tetrahydro-1-(p-tolylsulphonyl)benz[c,d]indol-5-one (7.5 gms, 0.019 m) and 1,3-propanedithiol (4.3 gms, 0.039 m) in chloroform (100 ml) is added a solution of trimethylsilylchloride (4.3 gms, 0.039 m) in chloroform. After stirring at room temperature for 72 hours, the white solid is collected by filtration to yield 4.9 gms of 4-acetamino-1,3,4,5-tetrahydro-1-(p-tolylsulphonyl)benz[c,d]indol-5-one(1,3-propylenedithic Ketal), m.p. 162°-166°.

Step C: 4-Acetamino-1,3,4,5-tetrahydro-1-(p-tolylsulphonyl) benz[c,d]indole

To a stirred suspension of activated Raney-nickel (30 gms) in absolute ethanol (300 ml) is added 4-acetamino-1,3,4,5-tetrahydro-1-(p-tolylsulphony)benz[c,d]indol-5-one (1,3-propylenedithio Ketal) (4.0 gms). The resulting mixture is refluxed for 17 hours. The reaction mixture is cooled, and the Raney-nickel is removed by filtration. The filtrate is concentrated under reduced pressure (20 mm) to yield 3.2 gms of (4-acetamino-1,3,4,5-tetrahydro-1-(p-tolylsulphonyl)benz[c,d]indole) which is used in the next step without further purification.

Step D: 4-(N-Ethylamino)-1,3,4,5-tetrahydrobenz[c,d]indole

To a slurry of lithium aluminum hydride (3.0 gm) in dry tetrahydrofuran (200 ml) is added 4-acetamino-1,3,4,5-tetrahydro-1-(p-tolylsulphonyl)benz[c,d]indole (3.0 gms). The resulting slurry is refluxed for 17 hours. After cooling, a solution of sodium potassium tartrate (40 gm) in water (100 ml) is added to the reaction mixture. The tetrahydrofuran layer is separated, and the aqueous solution is extracted with ether. The organic layers are combined and washed with a saturated aqueous sodium chloride solution (100 ml). After drying with anhydrous sodium sulfate, the solution is filtered and the organic solvents are removed under reduced pressure (20 mm) to yield an oil. The oil is purified by column chromatography (silica gel, chloroform saturated with ammonium hydroxide, 1% methanol) to yield 4-(N-ethylamino)-1,3,4,5-tetrahydrobenz[c,d]indole (540 mg).

Alternative Step D: 4-(N-Ethylamino)-1,3,4,5-tetrahydrobenz[c,d]indole hydrochloride To a slurry of lithium aluminium hydride(3 g)in dry THF is added 4-acetamino-1,3,4,5-tetrahydro-1-(p-tolylsulphonyl)benz[c,d]indole (3.0 gms). The resulting slurry is refluxed for 17 hours. After cooling, a solution of sodium potassium tartrate (40 gm) in water (100 ml) is cautiously added to the reaction mixture. The tetrahydrofuran layer is separated, and the aqueous solution is extracted with ether. The organic layers are combined and washed with a saturated aqueous sodium chloride solution (100 ml). After drying over anhydrous sodium sulfate, the solution is filtered and the organic solvents are removed under reduced pressure (20 mm) to yield an oil. The oil is dissolved in ether and the solid is filtered. To the ether solution is added an ethanolic hydrochloric acid solution. The solid is filtered and recrystallized from methanol-ether to yield 1.0 gm of 4-(N-ethylamino)-1,3,4,5-tetrahydrobenz[c,d]indole hydrochloride; melts 254°-256°.

Other compounds of the present invention which are prepared using the process substantial described in Example 1, substituting the acylating agent as indicated for the acetic anhydride, are tabulated below.

COMPOUNDS OF FORMULA

| Acylating Agent | R Group |
|---|---|
| (C₆H₅-CO)₂O (benzoic anhydride) | C₆H₅- |
| (CH₃-CH₂-CO)₂O | CH₃-CH₂- |
| Cl-C₆H₄-COCl | Cl-C₆H₄- |
| C₆H₅-CH₂-COCl | C₆H₅-CH₂- |
| CH₃O-C₆H₄-COCl | CH₃O-C₆H₄- |
| (C₂H₅-C₆H₄-CO)₂O | C₂H₅-C₆H₄- |

Where the compounds have a substituent ($R_2$) on the indole N, this derivative may be prepared by treating the 4-N-protected indole with an appropriate alkylating reagent such as methyl iodide in basic medium to obtain the corresponding indole N substituted compound.

Preparation of compounds of formula I where $R_1$ and/or $R_3$ are other than H, can be achieved by starting with an appropriately substituted compound of the formula A type. Using such appropriate $R_1$ and or $R_3$ substituted starting material the following compounds are prepared:

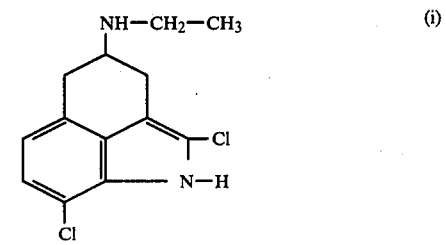

(i)

-continued

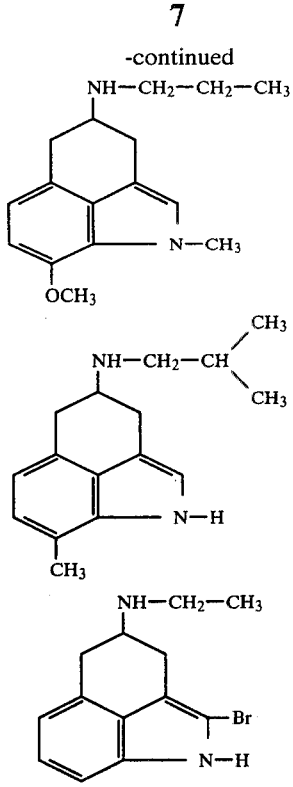

The compound (ii) may be converted to the corresponding compound where the group in the 8-position is OH by suitably cleaving the OCH$_3$ group by using e.g. trimethylsilyl iodide [see J. Org. Chem. 42, 3761–3764 (1977)].

Halogenation, of the tetrahydrobenzindole moiety in the 2-position can be carried out using the process described in von F. Troxler in Helv. Clinc. Acta 40, 2160 (1957).

Claims to the invention follow.
What is claimed is:

1. A pharmaceutical composition for treating hypertension containing an effective amount of a compound having the formula

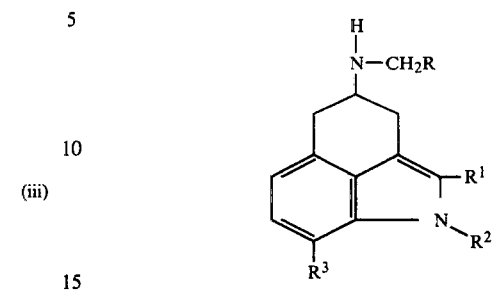

and pharmaceutically acceptable salts thereof wherein
R is H, alkyl having up to 6 carbon atoms, phenyl and monosubstituted phenyl wherein the substituent is halogen, C$_1$–C$_3$alkyl or C$_1$–C$_3$alkoxy,
R$^1$ is H or halogen,
R$^2$ is H, alkyl having up to 6 carbon atoms, phenyl-C$_1$–C$_3$alkyl or monosubstituted phenyl-C$_1$–C$_3$alkyl wherein the substituent is halogen, C$_1$–C$_3$alkyl or or C$_1$–C$_3$alkoxy, and
R$^3$ is H, OH, halogen, OCH$_3$ or C$_1$–C$_3$alkyl and pharmaceutically acceptable compounding ingredient.

2. A composition of claim 1 wherein said alkyl group is C$_1$–C$_3$alkyl.

3. A composition of claim 2 wherein R is said alkyl group.

4. A composition of claim 2 wherein R is CH$_3$.

5. A composition of claim 4 wherein R$^1$, R$^2$ and R$^3$ are all H.

6. A composition of claim 2 wherein R is said aryl group.

7. A pharmaceutical composition of claim 1 wherein in said compound R is CH$_3$ and R$^1$, R$^2$ and R$^3$ are all H.

8. A method of treating hypertension which comprises administering an effective amount of a composition of claim 1.

* * * * *